United States Patent [19]

Bertram et al.

[11] 4,056,658

[45] Nov. 1, 1977

[54] FOOD AND FODDER ADDITIVE

[75] Inventors: Heidrun Bertram, Grossauheim; Rudolf Fahnestich, Mombris; Joachim Hesse, Grossauheim, all of Germany

[73] Assignee: Deutsche Gold- und Silber-Scheideanstalt Vormals Roessler, Frankfurt, Germany

[21] Appl. No.: 408,051

[22] Filed: Oct. 19, 1973

[30] Foreign Application Priority Data

Oct. 23, 1972 Germany .............................. 2251877
Dec. 18, 1972 Germany .............................. 2261926

[51] Int. Cl.$^2$ .......................... A23J 3/00; A23K 1/00
[52] U.S. Cl. ...................................... 426/2; 426/630; 426/635; 426/656

[58] Field of Search .................... 424/177; 260/112.5; 426/630, 635, 656

[56] References Cited

PUBLICATIONS

Craft et al.: Chem. Abstr. 70:55572p (1969).
Matthews et al.: Chem. Abstr. 72:130,151x (1970).
Crampton et al.: Chem. Abstr. 73:1683u (1970).
Cheng et al.: Chem. Abstr. 75:2603w (1971).
Odorico et al.: Chem. Abstr. 69:94132u (1968).
Thier et al.: Chem. Abstr. 71:68356s (1969).
Smirnov: Chem. Abstr. 75:106868c (1971).

*Primary Examiner*—Delbert R. Phillips
*Attorney, Agent, or Firm*—Cushman, Darby & Cushman

[57] ABSTRACT

DL-methionyl-DL-methionine is prepared and used as a food and fodder additive.

11 Claims, No Drawings

FOOD AND FODDER ADDITIVE

The present invention is directed to the preparation of DL-methionyl-DL-methionine and its use in food and fodder.

DL-methionyl-DL-methionine, the dipeptide of DL-methionine having the formula

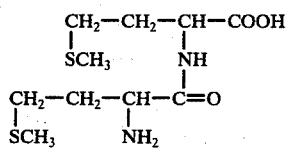

has not previously been described. It can be prepared in customary manner for making peptides, for example by reaction of N-carbobenzoxy-methionine with methionine ethyl ester and dicyclohexylcarbodiimide to form N-carbobenzoxymethionyl-methionine and removal of the N-carbobenzoxy group with an alkali metal, e.g., sodium or potassium, in liquid ammonia. This procedure, however, is expensive.

A superior process according to the invention for the production of DL-methionyl-DL-methionine is to saponify 3,6-bis(2'-methylmercaptoethyl)-2,5-diketopiperazine at a pH between 7 and 12.

3,6-bis(2'-methylmercaptoethyl)-2,5-diketopiperazine is produced by heating esters of methionine, for example methionine isopropyl ester to the boiling temperature. If the saponification of the bis-methylmercaptoethyl-diketopiperazine is carried out under customary conditions for this type of saponification, by mixing the bis-methylmercaptoethyl-diketopiperazine with an equivalent amount of alkali hydroxide, e.g., sodium hydroxide or potassium hydroxide, and then heating the mixture, the bis methylmercaptoethyl-diketopiperazine is saponified in only small amounts to methionyl methionine, but instead is saponified essentially to methionine. In contrast by keeping the pH between 7 and 12, preferably between 9.0 and 11.5, especially between 10.0 and 10.8 there is obtained methionyl-methionine in high yields. Surprisingly the methionyl-methionine produced in this manner is of excellent purity and in distinction from pure methionine is completely odorless and tasteless.

As saponification agents there can be used substances which are suitable for installing the desired pH value in the saponification medium. Thus there can be used ammonia, basically acting alkali salts, e.g., alkali carbonates such as sodium carbonate and potassium carbonate, and alkali hydroxides, preferably potassium hydroxide and sodium hydroxide. The saponification agent is preferably added as aqueous or alcoholic solutions, e.g., the solvent is water, methyl alcohol, ethyl alcohol or isopropyl alcohol.

For the saponification the bis-methylmercaptoethyl-diketopiperazine is advantageously added as a suspension or solution in an inert organic solvent, especially alcohols such as methanol, ethanol, propanol, isopropanol, n-butanol or ethylene glycol or in mixtures of these solvents with water, preferably in water alone. The water needed for the saponification is a given case can in a given case be introduced completely or partially by using the saponification agent as an aqueous solution.

The saponification can take place at normal pressure, if need be also at reduced pressure or superatmospheric pressure. Generally there are not used temperatures below about 50° C. and not over about 180° C. The preferred temperatures are between about 65° and 140° C., especially between 90° and 120° C.

There is needed an amount of saponification agent equivalent to the bis-methylmercaptoethyl-diketopiperazine. It is possible to use an excess of saponification agent up to about 5%, however, it is advantageous to add the saponification agent in at most an equivalent amount or in a slight deficiency. Preferably there is used 0.95 to 1.00, especially 0.98 to 1.00 equivalent of the saponification agent per equivalent of the diketopiperazine.

During the carrying out of the saponification the pH is constantly held in the stated range of 7 to 12. This means generally that the saponification agent is only added gradually to the composition, in which it is used for the saponification. Preferably, there always should be present less saponification agent than is equivalent to the amount of dissolved bis-methylmercaptoethyl-diketopiperazine present.

To recover the methionyl-methionine from the saponification mixture the pH of the mixture is adjusted to about 5.6. The methionyl-methionine which crystallized out is separated by centrifuging or filtration.

The DL-methionyl-methionine is used as a food or fodder additive, e.g., for cattle or sheep. It can be used in any place in which there is required a difficulty water soluble, but easily alkali soluble derivative of methionine which besides is odorless and tasteless. After taking up the methionyl-methionine with the food the methionine is soon set free and is then available unhindered for protein synthesis in the organism.

Unless otherwise indicated all parts and percentages are be weight.

EXAMPLE 1

131 grams (0.5 mole) of 3,6-bis(2'-methylmercaptoethyl)-2,5-diketopiperazine was first stirred into a paste with 250 ml of water and then mixed with a further 750 ml of water. The suspension thus formed was heated and held at the boiling temperature under reflux. Then in the course of 6 hours there were gradually added dropwise 0.5 mole of sodium hydroxide in 10% aqueous solution at such a slow rate that the pH did not exceed 10.8. The mixture was subsequently held for 30 minutes at the boiling temperature, then cooled and clarified by the addition of 10 grams of activated carbon, subsequently concentrated to a volume of 600 ml by evaporation under reduced pressure, adjusted to a pH of 10.5 by addition of sulfuric acid and filtered with suction. There were recovered 13.6 grams of unreacted 3,6-bis(2'-methylmercaptoethyl)-2,5-diketopiperazine. The filtrate was adjusted to a pH of 5.6 by the addition of sulfuric acid and then kept at room temperature with stirring for 2 hours. The DL-methionyl-methionine which separated was filtered with suction and then washed with 100 ml of water. There was recovered 90.0 grams corresponding to a yield of 65% based on the 3,6-bis(2'-methylmercaptoethyl)-2,5-diketopiperazine added. The DL-methionyl-DL-methionine was identified mass spectroscopically. As was established by thin layer chromatography the product was homogeneous, it melted between 221° and 255° C. with decomposition and was odorless and tasteless. The elemental analysis was

|  |  | C | H | N | S |
|---|---|---|---|---|---|
| $C_{10}H_{20}N_2O_3S_2$ | calculated | 42.9% | 7.1% | 10.0% | 22.8% |
|  | found | 42.9% | 7.3% | 10.4% | 22.5% |

EXAMPLE 2

The procedure of example 1 was followed but there was used 39.3kg (150 mole) of 3,6-bis(2'-methylmercaptoethyl)-2,5-diketopiperazine in altogether 310 liters of water and 180 liters of an aqueous 9.3% potassium hydroxide solution. After the feeding in of the potassium hydroxide was ended the mixture was treated with 1 kg of activated carbon and held for one hour at the boiling temperature, after the filtered at 65° C. over a filter press, then concentrated to 200 liters, cooled, adjusted to a pH of 5.6 with sulfuric acid and subsequently allowed to stand for 4 hours. The DL-methionyl-DL-methionine was filtered off with suction and dried under reduced pressure at 60° C. There was recovered 26 kg, corresponding to a yield of 62%. The methionyl-methionine had the same properties as that produced in example 1.

As stated previously the DL-methionyl-DL-methionine is useful as a food and fodder additive, e.g., as a source of methionine.

It is known that most proteins have an aminoacid composition which does not correspond to the composition of an ideal food-protein for humans or animals. In most cases one or more essential aminoacids are present in too little an amount. These aminoacids then limit the nutrition value of the protein. They are known as limiting proteins. This means that a substantial percentage of the food protein cannot be used to build suitable proteins because of the lack of an essential aminoacid from the body.

Thus it is known for example that soybean protein only has a biological value of 60 to 70 compared to the biological value of the complete egg protein. In this case methionine is the limiting protein. However, it is known that the biological value of protein can be improved considerably by addition of limiting aminoacid. Thus the addition of 1.2% of methionine based on the pure soya protein effects an increase in the biological value to nearly 85. This results from feeding experiments with rats in which the Protein-Efficiency Rate (PER) was increased from 2.37 to 3.21 (M. Swaminathan et al, J. Nutr. & Dietet., (1958) Vol. 5, page 323). This is also true for other food and fodder proteins such as peas and peanuts as well as for proteins from microfungi, bacteria or yeasts.

In all of these cases the addition of methionine is possible to only a limited extent however because of the easy solubility in water of this aminoacid. Since today many foods and fodders are treated with water before feeding or before consumption there is the danger that the supplementary aminoacid is again dissolved out. This is true in especial compositions for proteins which are manufactured to resemble meat products, as the materials known in commerce today as "textured — vegetable — proteins" (TVP).

In this process the protein, which for example can be obtained from soybeans or microorganisms is dissolved in alkali and forced through a nozzle into an acid bath so that a protein fiber is formed which can be combined through meatable treatment to meat-like structures. In the precipitation of the protein fibers in an acid bath the added methionine is again dissolved out so that the desired effect cannot be produced in this manner.

It is of course known to produce difficulty soluble addition salts of basic aminoacids with fatty acids (German Offenlegungschrift No. 2,036,163). However, it is not possible to obtain a difficulty soluble methionine derivative by this process.

One of the objects of the invention as indicated above is to develop an alkali soluble methionine derivative which is largely insoluble in water or dilute acid. On the other hand, however, the bound methionine after consumption should again be available largely for protein synthesis. With the help of DL-methionyl-DL-methionine in all cases it is possible to have the properly required enrichment of methionine in proteins. The DL-methionyl-DL-methionine therefore can be used with especial advantage as a food or fodder additive. Its solubility in water is about 0.1g/100ml of water.

Surprisingly it has been found that the methionine activity of this dipeptide is practically equal to that of free methionine although it is probably a mixture of the 4 isomers L-methionyl-L-methionine, L-methionyl-D-methionine, D-methionyl-L-methionine and D-methionyl-D-methionine. Since peptides of D-aminoacids do not occur in nature it was rather to be expected that this peptide could not be utilized and that therefore the total acticity of DL-methionyl-DL-methionine would be considerably less than the activity of free methionine.

A further important advantage which is connected with the use of the invention is the fact, as stated above, that in contrast to methionine DL-methionyl-DL-methionine is odorless and tasteless which is of especial advantage in the use of the substance as an additive for food and fodder.

The amount of this compound added to a protein is adjusted according to the total content of sulfur containing aminoacids in the concerned protein. Commonly, the methionine content in the field contributed by the added DL-methionyl-DL-methionine is about 0.1 to 1% based on the crude protein content.

Thus the protein in the feed can be the protein of soybean, peas, yeast or other microorganisms.

EXAMPLE 3

In a 4 week feeding experiment three groups of four 21 to 24 day old albino rats (SIV 50) were held on the following diet.

Group 1: Basal diet (methionine deficient ration)
Group 2: Basal diet +0.1% DL-methionine *
Group 3: Basal diet +0.094% DL-methionyl-DL-methionine *

* based on the content of crude protein

The methionine deficient ration had the following composition:

| | |
|---|---|
| Soyabean pieces (50% raw protein) | 20% |
| Rice starch (DAB 6) | 66% |
| Soybean oil (refined) | 2% |
| Cellulose | 4% |
| Mineral Mixture | 6% |
| Vitamin mixture (on rice starch) | 2% |
| | 100% |

The results are shown in the following table:

| Group | Initial Weight*) g | Final Weight*) g | Increase in Weight*) based on the Initial Weight g | % |
|---|---|---|---|---|
| 1 | 200 | 548 | 348 | 174 |
| 2 | 194 | 732 | 538 | 277 |
| 3 | 198 | 728 | 530 | 267 |

*) Total weight of the 4 rats in the group

We claim:

1. A protein containing feed deficient in methionine containing DL-methionyl-DL-methionine in an amount sufficient to eliminate the deficiency.

2. A protein containing feed according to claim 1 wherein the DL-methionyl-DL-methionine content sufficient to supply 0.1 to 1% of methionine based on the total protein present.

3. A protein containing feed according to claim 2 wherein the protein is soya protein, yeast protein or pea protein.

4. Soya protein having admixed therewith DL-methionyl-DL-methionine.

5. A feed according to claim 2 which is fodder.

6. A feed according to claim 1 which is fodder.

7. A process of supplying methionine to an animal comprising feeding the animal DL-methionyl-DL-methionine.

8. A process according to claim 7 wherein the DL-methionyl-DL-methionine is supplied together with fodder.

9. A process according to claim 7 wherein the DL-methionyl-DL-methionine is supplied together with a protein.

10. A process according to claim 9 wherein the protein is soya protein; yeast protein or pea protein.

11. A process according to claim 7 wherein the animal is cattle or sheep.

* * * * *

UNITED STATES PATENT OFFICE
CERTIFICATE OF CORRECTION

Patent No. 4,056,658          Dated November 1, 1977

Inventor(s) Heidrun BERTRAM, Rudolf FAHNENSTICH, Joachim HEESE

It is certified that error appears in the above-identified patent and that said Letters Patent are hereby corrected as shown below:

[75]    Second inventor should be:

Rudolf Fahnenstich

*Signed and Sealed this*

*Twenty-first* Day of *February 1978*

[SEAL]

*Attest:*

RUTH C. MASON          LUTRELLE F. PARKER
*Attesting Officer*      *Acting Commissioner of Patents and Trademarks*